US006649628B1

(12) United States Patent
Kürthy et al.

(10) Patent No.: US 6,649,628 B1
(45) Date of Patent: Nov. 18, 2003

(54) N-[2-HYDROXY-3-(1-PIPERIDINYL) PROPOXY]PYRIDINE-1-OXIDE-3-CARBOXIMIDOYL CHLORIDE AND ITS USE IN THE TREATMENT OF INSULIN RESISTANCE

(75) Inventors: Maria Kürthy, Balatonfüred (HU); Katalin Bíró, Budapest (HU); Károly Nagy, Budapest (HU); László Ürögdi, Budapest (HU); Zita Csákai, Kunszentmiklós (HU); Jenö Szilbereky, Budapest (HU); Tamás Mogyorósi, Kazincbarcika (HU); Magdolna Török, Mátészalka (HU); András Komáromi, Veszprém (HU); Ede Márványos, Budapest (HU); Mihály Barabás, Budapest (HU); Mihályné Kardos, Veszprém (HU); Zoltán Nagy, Budapest (HU); László Korányi, Budapest (HU); Melinda Nagy, Veszprém (HU)

(73) Assignee: Biorex Kutato es Fejleszto RT, Veszprem-Szabadsagpuszta (HU)

( * ) Notice: Subject to any disclaimer, the term of this patent is extended or adjusted under 35 U.S.C. 154(b) by 0 days.

(21) Appl. No.: 09/913,263
(22) PCT Filed: Feb. 24, 2000
(86) PCT No.: PCT/HU00/00015
§ 371 (c)(1),
(2), (4) Date: Dec. 18, 2001
(87) PCT Pub. No.: WO00/50403
PCT Pub. Date: Aug. 31, 2000

(30) Foreign Application Priority Data

Feb. 26, 1999 (HU) ............................................. P9900475

(51) Int. Cl.$^7$ ..................... A61K 31/445; C07D 211/06
(52) U.S. Cl. ....................................... 514/318; 546/193
(58) Field of Search ........................... 514/318; 546/193

(56) References Cited

U.S. PATENT DOCUMENTS

| 5,328,906 A | 7/1994 | Nagy et al. .............. 514/235.5 |
| 6,268,309 B1 * | 7/2001 | Nagy et al. ................. 504/223 |

FOREIGN PATENT DOCUMENTS

| WO | WO 90/04584 | 5/1990 |
| WO | WO 97/16439 | 5/1997 |
| WO | WO 98/43948 | 10/1998 |
| WO | WO 01/79174 | * 10/2001 |

OTHER PUBLICATIONS

Wyngaarden et al. "Cecil Texbook of medicine" Saunders Co. p. 1059–1065 (1983).*

* cited by examiner

Primary Examiner—Ceila Chang
(74) Attorney, Agent, or Firm—Finnegan, Henderson, Farabow, Garrett & Dunner, L.L.P.

(57) ABSTRACT

N-[2-hydroxy-3-(1-piperidinyl)-propoxy]-pyridine-1-oxide-3-carboximidoyl chloride, its stereoisomers, and the addition salts thereof, pharmaceutical compositions containing the same, methods of treating pathological insulin resistance, methods of treating pathological insulin resistance and pathological conditions associated therewith, and methods of treating pathological insulin resistance by simultaneously treating diabetes-induced chronic complications, especially retinopathy, neuropathy and nephropathy, and/or by simultaneously increasing pathologically decreased peripheral neuroregeneration caused by diabetes.

10 Claims, No Drawings

N-[2-HYDROXY-3-(1-PIPERIDINYL) PROPOXY]PYRIDINE-1-OXIDE-3-CARBOXIMIDOYL CHLORIDE AND ITS USE IN THE TREATMENT OF INSULIN RESISTANCE

This application is a 371 of PCT/HU00/00015 filed Feb. 24, 2000.

An O-(3-piperidino-2-hydroxy-1-propyl) hydroxymic acid halide derivative, its application in the treatment of insulin resistance, and the pharmaceutical preparation containing this derivative as effective agent.

TECHNICAL FIELD OF THE INVENTION

The invention relates to an O-(3-piperidino-2-hydroxy-1-propyl) hydroxymic acid halide derivative, the pharmaceutical use thereof and the pharmaceutical products containing this derivative as active ingredient. Namely, the invention relates to N-[2-hydroxy-3-(1-piperidinyl)-propoxy]-pyridine-1-oxide-3-carboximidoyl chloride, its stereoisomers, as well as their acid addition salts. Furthermore, the invention also relates to the use of these compounds in the treatment of insulin resistance and the pharmaceutical products containing these derivatives as active ingredient.

BACKGROUND OF THE INVENTION

O-(3-piperidino-2-hydroxy-1-propyl) hydroxymic acid halide derivatives are already known from European Patent Specification No. 0 417 210 B1. According to this patent specification, these compounds exhibit a selective beta blocking effect and are thus suitable for the treatment of diabetic angiopathy, more specifically, of diabetic retinopathy and nephropathy.

According to PCT Publication WO 98/06400, the O-(3-piperidino-2-hydroxy-1-propyl) hydroxymic acid halide derivatives and other compounds of similar structure are effective in protecting and regenerating vascular endothelial cells, and are thus suitable active agents for the treatment of diseases caused by the dysfunction of the endothelium.

The chaperon-expression increasing effect of several hydroxylamine derivatives. among them of the O-(3-piperidino-2-hydroxy-1-propyl) hydroxymic acid halides, and the use of these, compounds in the treatment of diseases connected with the functioning of the chaperon system are known from WO 97/16439. In this patent application, O-(3-piperidino-2-hydroxy-1-propyl)-3-pyridyl hydroxymic acid chloride N-oxide derivatives (among others) are defined and claimed as new compounds, however, the production procedure is only described for piperidine-N-oxide and for the compound containing N-oxide groups both in the piperidine and pyridine rings. The compound of the present invention is not mentioned in the above application.

Insulin resistance is a pathological condition that blocks the effects of insulin. It is generally associated with diabetes, although its formation is also possible independently. Due to insulin resistance, the body needs higher and higher concentrations of insulin for carbohydrate, lipid and protein metabolism, which leads to an extremely high concentration of insulin. A long-lasting high insulin concentration has been proven to be an independent cardio-cerebro-vascular risk factor.

The reduction of insulin resistance is essential in both types of diabetes: in case of diabetes type 2, it is present as a major ethiological factor, while in case of diabetes type 1, insulin resistance is caused by glucose toxicity as well as excessive amounts of insulin applied exogenously for therapeutical purposes.

Several active agents have been provided for the reduction of insulin resistance. Among these, the most significant ones are the insulin sensitizer products, the best known agent therefrom being troglitazone, a member of the thiazolidine-dione group. (A. R. Saltiel et al., Diabetes 45/12/1996 pp. 1661–1669, and S. Kumar et al., Diabetologia 1996/39/6 pp. 701–709). The main effect of this compound is the reduction of insulin resistance by lowering peripheral insulin concentrations both in basal state and after glucose stimulation. As a result, it improves carbohydrate metabolism as well as corrects a number of pathological deviations arising as the secondary effect of high insulin level, such as hyperlipidaemia and pathological hemostasis. Its ultimate positive effect is the reduction of the cardiovascular risk. A. disadvantage is, however, that it may cause serious, mainly hepatotoxic side effects therefore its application is limited and requires due caution.

SUMMARY OF THE INVENTION

During studies in the area of O-(3-piperidino-2-hydroxy-1-propyl) hydroxymic acid halides, detailed examination of the maleate of O-(3-piperidino-2-hydroxy-1-propyl)-3-pyridyne hydroxymic acid-chloride, known as bimoclomol has been performed and found that its most significant effect is on the pathological consequences of chronic neuropathy: it significantly improves motoric and sensory nerve conduction velocity deficits in diabetes, and also favorably effects pathological deviations resulting from autonomous neuropathy. Furthermore, both in animal experiments and in phase II tests on humans, it reduces pathological diabetic urinary albumin excretion, and in the animal tests it reduces pathological histological and electrophysiological alterations resulting from diabetic retinopathy. However, in the reduction of insulin resistance bimoclomol was not effective.

At present, no medicinal products are available which could reduce insulin resistance and at the same time effectively cure deviations resulting from all three chronic diabetic complications.

In a search for suitable active materials, N-oxide derivatives of bimoclomol were tested for biological acitvity. In a preliminary test the effectiveness of the three N-oxide derivatives of bimoclomol on motor and sensor neuropathy in STZ diabetic Wistar rats were studied. The effectiveness of the three bimoclomol N-oxide derivatives in improving the peripheral motor and sensor nerve conduction velocity deficit caused by streptozotocine-induced diabetes was determined with use of the method described in detail in Experiment 2. The results are summarized in the following table.

| Group | n | Improvement of nerve conduction velocity (%) | |
| --- | --- | --- | --- |
| | | motor (MNCV) | sensor (SNCV) |
| bimoclomol 20 mg/kg | 7 | 72,4 | 66,9 |
| pyridine N-oxide derivative of bimoclomol 5 mg/kg | 8 | 66,5 | 63,4 |
| piperidine N-oxide derivative of bimoclomol 5 mg/kg | 8 | 34,7* | 27,3** |
| double N-oxide derivative of bimoclomol 5 mg/kg | 8 | 25,9* | 29,1** |

*p < 0,05 related to bimoclomol
**p < 0,01 related to bimoclomol

As it appears from the above results, the pyridine N-oxide derivative of bimoclomol is equivalent with bimoclomol while the two other N-oxide derivatives have significantly weaker effect on the motor and sensor neuropathy. Based on this experience, investigations were continued with the pyridine N-oxide derivative of bimoclomol, namely N-[2-hydroxy-3-(1-piperidinyl)-1-propoxy]-pyridine-1-oxide-3-carboximidoyl chloride.

Our investigations yielded the unexpected result that N-[2-hydroxy-3-(1-piperidinyl)-propoxy]-pyridine-1-oxide-3-carboximidoyl chloride reduces peripheral insulin resistance in addition to exhibiting an effect equal to or in some cases greater than that of bimoclomol in the treatment of the above mentioned three main diabetic complications. Due to this characteristic, the compound is suitable for the treatment of chronic diabetic complications, especially of retinopathy, neuropathy and nephropathy, and for the simultaneous reduction of peripheral insulin resistance, but it is also suitable for the treatment of non-diabetic pathological insulin resistance and any pathological conditions related to it.

The favorable biological properties of N-[2-hydroxy-3-(1-piperidinyl)-propoxy]-pyridine-1-oxide-3-carboximidoyl chloride were proven by the following experiments. For these tests, the maleate of N-[2-hydroxy-3-(1-piperidinyl)-propoxy]-pyridine-1-oxide-3-carboximidoyl chloride or the maleate of the suitable optically active compound were used as test compounds. In the description of the experiments, the maleate of the racemic compound is referred to as Compound A, while the maleate of the optically active stereoisomer is always specifically indicated.

EXPERIMENT 1
Effect of Treatment by Compound A and Bimoclomol on Carbohydrate Metabolism in Obese, Insulin Resistant, Hyperinsulinaemic Zucker fa/fa Rats with Impaired Glucose Tolerance, Following a 2-Month Treatment.

Materials and Methods
In the experiments so-called Zucker fa/fa rats (Charles River Laboratories Inc.) were used. In monozygotic animals, obesity, insulin resistance, high blood insulin level, impaired glucose tolerance and hypertriglyceridaemia result from hypothalamic leptin receptor mutation. Due to the above characteristics, this is an accepted model of early type 2 diabetes.

The animals were placed in individual metabolic cages for 24 hours at the beginning of the study, and after 1 or 2 months of treatment for 24 hours of urine collection.

The animals were given either the test substances or physiological saline solution by gavage for control once a day between weeks 14–22.

Biochemical parameters of the blood and the urine were measured by a Kodak Ectachem 700 automatic analyzer. The total protein level of the urine was determined spectrophotometrically with the use of Bradford staining (Hitachi U-3200) at 595 nm. The insulin concentration of the serum was determined by the RIA method, using rat anti-insulin antibodies.

Systolic, diastolic blood pressure and heart rate were measured weekly on the tails of the rats (so-called tail cuff method) by a Letica 200 automatic analyzer. After two months of treatment, the level of glucose tolerance was determined by the intraperitoneal glucose tolerance test (2 g/kg ip.).

Results
Bimoclomol administered in daily doses of 20 mg/kg p.os significantly reduced the level of fasting blood glucose, however, it did not effect the fasting insulin concentration.

In comparison with previous data, the unexpected outcome was that Compound A administered in daily doses of 20 mg/kg p.os significantly reduced both fasting blood glucose and insulin concentrations, the latter by approx. 50%. The results are given in Table 1 and FIG. 1.

TABLE 1

The Effect of Compound A and Bimoclomol on Fasted Blood Glucose and Insulin Concentrations

| | Fasting Blood Glucose (mmol/l) (mean ± SE) | Fasting Insulin (ng/ml) (mean ± SE) |
|---|---|---|
| Lean control | 7.197 ± 0.315** | 3.727 ± 0.302*** |
| Obese control | 9.774 ± 0.342 | 22.882 ± 3.790 |
| Compound A | 8.267 ± 0.436** | 11.176 ± 1.955** |
| Bimoclomol | 8.179 ± 0.316*** | 29.362 ± 9.211 |

$p < 0.001$, *$p < 0.0001$, compared to the Obese Control

In the course of the intraperitoneal glucose tolerance test, neither bimoclomol, nor Compound A effected the areas under the blood glucose curve (AUC). However, in case of the AUC of insulin there is a difference between the two compounds: bimoclomol had no effect, while Compound A reduced it significantly, to the same level as the Lean control. The results are given in Table 2 and FIG. 2.

The table contains the values of the area under the curve (AUC) between 0–60 minutes.

TABLE 2

The Effect of Treatment by Bimoclomol and Compound A on the Glucose Tolerance of Obese, Insulin Resistant, Hyperinsulinaemic Zucker fa/fa Rats with Impaired Glucose Tolerance, Following a 2-Month Treatment

| | Blood Glucose (AUC) (mean ± SE) | Insulin (AUC) (mean ± SE) |
|---|---|---|
| Lean control | 823.69 ± 60.66*** | 599.49 ± 86.76*** |
| Obese control | 1417.00 ± 159.88 | 1986.34 ± 213.84 |
| Compound A | 1418.40 ± 194.57 | 790.35 ± 166.08*** |
| Bimoclomol | 1286.86 ± 131.59 | 2337.71 ± 590.49 |

***$p < 0.0001$, compared to the obese control

Summary
Compound A significantly reduces peripheral insulin resistance, while bimoclomol does not.

EXPERIMENT 2
The Effect of Treatment by Compound A and Bimoclomol on the Pathological Deviations Resulting from Peripheral Neuropathy in STZ-Diabetic Wistar Rats, Following a 1-Month Treatment.

Materials and methods:
In the experiments, male Wistar rats were used (Charles River Laboratories Inc.). At the start of the experiment, their weights were 340–370 g. Diabetes was induced by the intravenous administration of a single 45 mg/kg dose of streptozotocine (STZ, Sigma, St. Louis, Mo.) dissolved in physiological saline solution. The development of diabetes was checked after 1 day by a blood glucose test, accepting a value over 15 mmol/l.

The test and reference substances were administered p.os to the animals once a day.

For the determination of nerve conduction velocity (NCV), the method of Stanley, modified by De Konig and Gispen was used. The animals were anesthetized by the simultaneous administration of Hyponorm (1 mg/kg ip., Janssen, Tilburg, Denmark), fluanisone (10 mg/ml), and phentanyl citrate (0.2 mg/ml). Afterwards, the left ischiadicus and tibial nerves were stimulated at standard points.

Supramaximal stimulus (square impulse, 0.03 ms) was used with a platinum needle electrode, through a Nihon-Kohden (model SEN-1104, Japan) stimulator. The electromyogram (EMG) transferred from the sole muscles and intensified by a myograph (Elema-Schonander, Stockholm, Sweden) was analyzed further by the Matlab for Windows (Mathwork Inc, UK) program. The extent of NCV damage caused by diabetes was expressed in m/s. The effectiveness of the treatment was compared to this in terms of percentage (%). The statistical calculations were done by unpaired t-test or single-criterion ANOVA test (along with the Newman-Keuls post hoc test). (Graphpad Instat, San Diego, Calif.).

Results

Bimoclomol administered once a day in a dose of 20 mg/kg and Compound A administered once a day in a dose of 5 mg/kg significantly improved motor (MNCV) and sensor (SNCV) nerve conduction velocities to the same significant extent in diabetic animals. An increase in the dose of Compound A over 10 mg/kg did not increase the effect. The results are given in Table 3.

TABLE 3

The Effect of Treatment by Compound A and Bimoclomol on the Nerve Conduction Velocity (NCV) Deficit of STZ-Diabetic (STZ-DB) Wistar Rats

| | Nerve Conduction Velocity (NCV) | | | |
|---|---|---|---|---|
| | MNCV | | SNCV | |
| Group | m/s | improvement % | m/s | improvement % |
| Control | 60.9 ± 0.2 | | 62.3 ± 0.3 | |
| STZ-DB control | 43.7 ± 0.2 | | 44.7 ± 0.2 | |
| STZ-DB + bimoclomol 20 mg/kg | 57.4 ± 0.2*** | 79.7 | 58.5 ± 0.6*** | 77.9 |
| STZ-DB + Compound A | | | | |
| 5 mg/kg | 57.4 ± 0.3*** | 79.5 | 58.4 ± 0.3*** | 77.6 |
| 10 mg/kg | 59.2 ± 0.3*** | 90.4 | 60.4 ± 0.4*** | 89.0 |
| 20 mg/kg | 59.1 ± 0.3*** | 89.8 | 60.1 ± 0.3*** | 87.4 |

***$p < 0.001$

EXPERIMENT 3
The Effect of Treatment by Compound A and Bimoclomol on the Pathological Deviations Resulting from Diabetic Autonomous Neuropathy in STZ-Diabetic Wistar Rats, after 1 Month of Treatment.

Materials and Methods

In the experiments, male Wistar rats were used (Charles River Laboratories Inc.), at the start of the experiment their weights were 340–370 g. Diabetes was induced by the intravenous administration of a single 45 mg/kg dose of streptozotocine (STZ, Sigma, St. Louis, Mo.) dissolved in physiological saline solution. The development of diabetes was checked after 1 day by a blood glucose test, accepting a value over 15 mmol/l.

The test and reference substances were administered p.os_to the animals once a day.

The experiments were performed under anesthesia achieved by administering 60 mg/kg ip. pentobarbital sodium (Nembutal, Sanofi, Phylaxia). After this, an intratracheal tube or polyethylene canula was inserted into the fermoral artery and vein. The arterial catheter was connected to a pressure transducer for the simultaneous measurement of systolic and diastolic blood pressure (online automatic measuring and forwarding system, with a Haemosys computer program). After 20 minutes of equillibration period, the following substances were administered intravenously: Noradrenalin, 5 µg/kg iv.—Isoproterenol 0.4 µg/kg iv.— N.vagus stimulation (2 V, duration: 500 µsec, delay: 1 msec). The effects of the substances were monitored for 10 minutes.

Results

Autonomous neuropathy is one of the leading causes of sudden cardiac death both in the case of diabetes and of other diseases (e.g. liver diseases). Therefore, all products that can effectively reduce pathological deviations resulting from autonomous neuropathy are very important.

In the experiments, a daily 20 mg/kg single dose of either bimoclomol or Compound A significantly reduced several pathological deviations resulting from autonomous neuropathy.

A summary and comparison of our results are shown in Table 4.

The double arrow in the Table indicates that the test substance is statistically more effective than the other one.

TABLE 4

| Deviation due to diabetes | Bimoclomol | Compound A |
|---|---|---|
| Systemic arterial hypotension | ↑ | ↑↑ |
| Weight loss | ↑ | ↑↑ |
| Heart left ventricular hypertrophy | ↑↑ | ↑ |
| Reduced NA induced systemic arterial pressure response | ↑ | ↑↑ |
| Reduced IS induced systemic arterial hypotension | ↑ | — |
| Reduced IS induced positive chronotropic effect | ↑ | ↑↑ |
| Increased negative chronotropic effect on vagus stimulation | ↑ | ↑ |
| Reduced hypotension on vagus stimulation | ↑ | ↑ |

NA:noradrenaline
↑:corrects
IS:isoproterenol
—:ineffective

EXPERIMENT 4
The Effect of Treatment by Compound A and Bimoclomol on the Pathological Histological Alterations Caused by Early Diabetic Retinopathy in STZ-Diabetic Wistar Rats, Following 1 Month of Treatment.

Materials and Methods
In the experiments, male Wistar rats were used (Charles River Laboratories Inc.), at the start of the experiment their weights were 340–370 g. Diabetes was induced by the intravenous administration of a single 45 mg/kg dose of streptozotocine (STZ, Sigma, St. Louis, Mo.) dissolved in physiological saline solution. The development of diabetes was checked after 1 day by a blood glucose test, accepting a value over 15 mmol/l.

The test and reference substances were administered p.os_to the animals once a day.

After anesthesia (Calypsovet, 125 mg/kg. Ip., Richter Rt., Hungary), the eyes were enucleated and fixed in 4% formaldehyde dissolved in a phosphate buffer (pH:7.4).

Afterwards, they were embedded in paraffin (Medim DDM P800, embedding center: Lignifer L-120-92-014, stainer: Shandon Eliott, Microtome: is Leica SM 2000 R, Microscope: Jenaval Karl Zeiss Jena). Several 6 micron sections of the eyes were prepared, and hematoxilyn/eosine (Fluka) and PAS (periodic acid-Schiff, Fluka) staining were used. The light-microscopic evaluation was performed at a magnification of 40× and 100×. Photographs and slide positives were prepared of representative samples.

The histological evaluation was performed on coded samples, the group division was unknown for the examiner. Pathological deviations of the retina were graded on a scale of 0–20, while those of the lens on a scale of 0–3.

The statistical calculations were done with the Statistica 4.5 (SatSoft, USA) program. The given value for negative cases was 0.1. A Box and Whisker plot graph was also prepared.

For each group in the experiment, the mean±SE (Standard Error) values were calculated, and the comparison was done with the help of a non-parametric Mann-Whitney U-test (Graphpad Instat, San Diego, Calif.).

Results

A daily single 5 mg/kg dose of Compound A and a daily single 20 mg/kg dose of bimoclomol significantly improved the diabetic retinopathy induced pathological histological alterations after 1 month of treatment. Of these two compounds, Compound A was statistically more effective in comparison with the diabetic, non-treated animals. The results are given in Table 5.

TABLE 5

The Effect of Treatment by Compound A and Bimoclomol on the Pathological Histological Alterations Caused by Early STZ-Diabetic Retinopathy

| | Score values | |
|---|---|---|
| Groups | Mean ± SE | Improvement % |
| Control | 1.785 ± 0.342 | 100 |
| STZ-diabetes | 10.571 ± 1.962 | |
| STZ-diabetes + 20 mg/kg bimoclomol | 5.185 ± 1.019* | 61.3 |
| STZ-diabetes + 5 mg/kg Compound A | 4.028 ± 0.961** | 74.5 |

$p < 0.05$ $p < 0.01$, compared to diabetic, non-treated animals.

EXPERIMENT 5

The Effect of Treatment by Compound A and Bimoclomol on Pathological Urinary Protein Loss Caused by Diabetic Nephropathy in STZ-Diabetic Wistar Rats, After a 1-Month Treatment.

Materials and Methods

In the experiments, male Wistar rats were used (Charles River Laboratories Inc.), at the start of the experiment their weights were 340–370 g. Diabetes was induced by the intravenous administration of a single 45 mg/kg dose of streptozotocine (STZ, Sigma, St. Louis, Mo.) dissolved in physibolgical saline solution. The development of diabetes was checked after 1 day by a blood glucose test, accepting a value over 15 mmol/l.

The test and reference substances were administered p.os_to the animals once a day.

For the 24-hour period of urine collection, the animals were placed in individual metabolic cages. During this period they were given water ad libitum but no food. The latter measure was necessary to prevent possible contamination by the protein content of the food. Urine was collected in calibrated glass containers, in which Thymol crystal (Reanal 3135-1-08-38) was placed to prevent bacterial contamination.

Before measurement, the urine samples were centrifuged (2500 rpm) and filtered through a paper filter (Whatmann 1). If necessary, they were stored at −20° C. until measurement.

The total protein content of the urine was determined by the Bradford staining method (Sigma B-6916, St. Louis, Mo.), and color intensity was detected by spectrophotometry (Hitachi-U-3200).

Results

Bimoclomol, administered in a daily single dose of 20 mg/kg, significantly reduced STZ-diabetes-induced elevated urinary protein loss. Compound-A, administered in a daily single dose of 10 mg/kg, non-significantly reduced protein loss. However, the (+) enantiomer of Compound A, administered in a daily single dose of 5 mg/kg significantly reduced diabetic protein loss. The results are given in Table 6.

TABLE 6

The Effect of Treatment by the (+) Enantiomer of Compound A and by Bimoclomol on the Urinary Protein Loss Caused by Diabetic Nephropathy in STZ-Diabetic Wistar Rats

| Group | 24-hour Urinary Protein Loss (mg/24 h) Mean ± SE |
|---|---|
| 1. | |
| STZ-diabetes | 8.302 ± 2.40 |
| STZ-diabetes + Bimoclomol, 20 mg/kg | 3.66 ± 1.39* |
| *$p < 0.05$ | |
| 2. | |
| STZ-diabetes | 13.03 ± 2.63 |
| STZ-diabetes + Compound A, 10 mg/kg | 12.06 ± 1.70 |
| STZ-diabetes + (+) enantiomer of Compound A, 5 mg/kg | 5.61 ± 1.08* |
| *$p < 0.02$ | |

EXPERIMENT 6

The effect of Compound-A and its (+) and (−) enantiomers on pathological alterations of peripheral neuropathy in STZ-diabetic Wistar rats after 1 month treatment.

Materials and methods: experimental animals and all the methods applied are the same as described in Experiment 2.

Results

Compound-A in a single daily dose of 10 mg/kg and Compound A(+) in a single daily dose of 5 mg/kg were equiactive and significantly improved both defective motor (MNCV) and sensory (SNCV) nerve conduction velocity deficits in diabetic animals. On the contrary, Compound A(−) did not have significant improving effect on either parameter. Results are shown in Table 7.

TABLE 7

The effects of Compound-A and its A(+) and A(−) enantiomers on nerve conduction velocity (NCV) deficits in STZ-diabetic Wistar rats

| | Nerve Conduction Velocity (NCV) | | | |
|---|---|---|---|---|
| | MNCV | | SNCV | |
| Group | m/s | improvement % | m/s | improvement % |
| Control | 62.7 ± 0.4 | | 64.9 ± 0.7 | |
| STZ-DB control | 46.9 ± 0.9 | | 48.4 ± 1.0 | |
| STZ-DB + Comp.A 10 mg/kg | 59.3 ± 0.3*** | 78.9 | 61.4 ± 0.7*** | 79.2 |
| STZ-DB + A(+) 5 mg/kg | 56.1 ± 0.5*** | 71.3 | 59.7 ± 0.5*** | 68.5 |
| STZ-DB + A(−) 5 mg/kg | 53.1 ± 0.7*** | 39.4 | 54.1 ± 0.9*** | 34.9 |

***$p < 0.001$ compared to STZ-diabetic non treated

EXPERIMENT 7

The effects of Compound-A and its A(+) and A(−) enantiomers on pathological histological alterations of early diabetic retinopathy in STZ-diabetic rats after 2 month treatment.

Materials and methods: the experimental animals and all the methods applied are the same as described in Experiment 4.

Results

The A(+) enantiomer in a single daily dose of 5 mg/kg significantly improved both lenticular and retinal pathologic histological alterations caused by diabetic retinopathy after 2 month treatment, while the effect of Compound-A in a single daily dose of 10 mg/kg was not significant and A(−) enantiomer in a single daily dose of 5 mg/kg was not effective. Regarding retinal histological alterations only, both Compound-A and its A(+) enantiomer were effective while the effect of the A(−) enantiomer was not significant. The results are shown in Table 8.

TABLE 8

The effects of Compound-A and its A(+) and A(−) enantiomers on histological alterations of early diabetic retinopathy in STZ-diabetic rats

| | Scores | | | |
|---|---|---|---|---|
| | lenticular + retinal | | retinal | |
| Groups | mean ± SE | improvement % | mean ± SE | improvement % |
| control | 0.56 ± 0.36 | 100 | 0.46 ± 0.36 | 100 |
| STZ-diabetic | 6.69 ± 0.76 | | 4.38 ± 0.68 | |
| STZ-DB + Comp.A 10 mg/kg | 4.55 ± 0.69 | 34.7 | 1.80 ± 0.75* | 65.8 |
| STZ-DB + A(+) 5 mg/kg | 4.05 ± 0.80* | 42.9 | 1.68 ± 0.63** | 68.9 |
| STZ-DB + A(−) 5 mg/kg | 6.02 ± 1.09 | 10.3 | 3.53 ± 1.07 | 21.7 |

*$p < 0.05$ compared to diabetic non-treated
**$p < 0.01$ compared to diabetic non-treated

EXPERIMENT 8

The effects of A(+) and A(−) enantiomers on in vivo insulin-dependent glucose uptake in dietary induced insulin resistant animal model.

Materials and Methods

Male Wistar rats (Charles River Laboratories Inc.) with an initial body weight of 300–350 g were used in the experiments.

Insulin resistance was induced by dietary manipulation: animals were given a high fat (HF) diet for 3 weeks. In the HF diet the proportion of saturated fats were dominant and gave 70% of total daily caloric intake. The A(+) and A(−) enantiomers were given once a day in preventive application in a dose of 20 mg/kg/day.

At the end of 3 weeks treatment the following parameters were investigated: 1 carbohydrate and lipid parameters from serum and 2, in vivo insulin-mediated glucose uptake by the euglycaemic glucose clamp method being currently the most accurate method for the quantitative determination of glucose uptake (DeFronzo et al., American Journal of Physiology, 1979/237/E214–223 pages). Briefly: the fasting blood glucose concentration in different animal groups must be identical. Experiments were carried out in conscious, freely moving, chronically canulated rats: first an insulin infusion (6.4 mU/kg/min) was started, followed by a parallel-run continuous glucose infusion to maintain blood glucose concentrations in the euglycaemic range. After stabilisation the quantity of infused glucose was measured for a 90 min. period (glucose infusion rate=GIR, mg/kg/min) which is the quantitative parameter of insulin sensitivity.

Results

The A(+) and A(−) enantiomers in a daily dose of 20 mg/kg/min did not affect the body weight and food consumption and the fasting blood glucose levels of the rats.

On the contrary both compounds normalized HF diet induced elevated fasting insulin and triglyceride concentrations and significantly decreased elevated muscle triglyceride content as well. The euglycaemic glucose clamp test revealed that HF diet significantly suppressed in vivo insulin mediated glucose uptake: control: 26.7+0.68 mg/kg/min, HF diet: 15.0+0.39 mg/kg/min. This suppressed insulin mediated glucose uptake is increased by both enantiomers: HF+ A(+): 20.5+0.89 mg/kg/min and HF+ A(−): 19.7+1.38 mg/kg/min (a significant increase in both cases at the level of $p<0.01$). According to these results both enantiomers increased the insulin-mediated glucose uptake which proves from a new perspective the insulin resistance reducing action of the compounds of the invention.

EXPERIMENT 9

The antidiabetic activity of A(+) enantiomer in Zucker Diabetic Fatty rats after chronic administration.

Materials and Methods

A genetically diabetic animal model was selected and the Zucker Diabetic Fatty (ZDF) rats were used in the experiments. This model is the diabetic variant of the insulin resistant, obese but non-diabetic Zucker fa/fa animal model (see Experiment 1). In the ZDF rats diabetes developed at the age of 6–8 weeks preceded by an insulin resistant phase. The effect of (A+) enantiomer was investigated in a treatment with a dose of 2×20 mg/kg/day started in the non-diabetic phase, at the age of 7 weeks and continued for 6 weeks.

Clinical chemistry parameters were measured by standard methods. The serum insulin concentrations were measured by a recently developed method (ELISA method, DRG lnternational,Inc., U.S.A.).

Results

It has been detected in this experiment as a new result that A(+) enantiomer has a strong antidiabetic activity in diabetic animals. Results obtained after 3 and 5 week treatment are shown in Table 9.

TABLE 9

| Fed serum glucose concentrations (mmol/l) | | |
|---|---|---|
| Groups | 3 weeks | 5 weeks |
| Control | 6.23 ± 0.08 | 5.87 ± 0.08 |
| ZDF | 18.56 ± 1.94 | 21.28 ± 1.65 |
| ZDF + A(+) 2 × 20 mg/kg | 10.82 ± 1.36* | 13.25 ± 0.76** |

*$p < 0.02$, **$p < 0.005$ compared to ZDF non treated

Though the treatment with A(+) enantiomer did not normalize blood glucose concentrations the combined effects of strong antidiabetic activity and the previously identified significant healing efficiency on chronic diabetic complications gives this compound a unique character. The therapeutic indication area of the A(+) enantiomer can be significantly broadened on the basis of this new combined efficiency.

Further experiments have led to the conclusion that the compounds of the invention, besides their efficacy on pathological complications of diabetes are useful in the treatment of other damages of peripheral nerves caused by diabetes. This conclusion is supported by the results of the following neuroregeneration experiment.

EXPERIMENT 10

The therapeutical effect of Compound-A and A(+) enantiomer on the neuroregeneration in STZ-diabetic Wistar rats.

Materials and Methods

The experiments were accomplished on Wistar rats with a body weight of 320–350 g. Diabetes was induced and checked as described in Experiment 2. In the test animals having been diabetic for 3 weeks the left nervus ischidiacus was injured by freezing and the right side one was used as non-injured control. The regeneration was observed by monitoring the signals of the flexor reflex provoked by irritation of the sole that is areas under curve (AUC) of the electromyogram transferred from the forward tibial muscle. For the stimulation and detection the system described in Experiment 2 was used. Single daily doses of 10 mg/kg of Compound-A and 5 mg/kg of A(+) enantiomer were administred for 5 weeks after the injury by freezing.

Results

In At the end of the 3 week period of diabetes, before the injury by freezing a sensor neuropathy developed and caused a 23–25% decrease in AUC on both legs. No response was observed during 2 weeks after the injury by freezing. The extent of neuroregeneration was 63% on the 5. week. The regeneration was enhanced to 73% by the Compound-A, the A(+) enantiomer was effective for an extent of 93%. Neuroregenerations of 83% and only 44% of the non-freezed nerves were observed as a result of treatment with A(+) enantiomer and Compound-A, respectively. Consequently, the A(+) enantiomer has a strong neuroregenerative effect.

N-[2-hydroxy-3-(1-piperidinyl)-propoxy]-pyridine-1-oxide-3-carboximidoyl chloride can be prepared by the following procedure, which is not known from the prior.

According to the oxidation method described in WO 97/16349, a derivative oxidized on the nitrogen atom of both rings, or with less reagent a derivative oxidized on the alicyclic ring can be prepared from O-(3-piperidino-2-hydroxy-1-propyl)-3-pyridine hydroxymic acid-chloride, since the alicyclic nitrogen atom is preferred in the oxidation reaction. The regioselectivity of the oxidation had to be directed towards the pyridine ring for the production of compound of the invention, therefore the procedure was modified. The main point of the modification is that, in order to facilitate the selective oxidation of the pyridine ring; the peracidic oxidation is performed in the presence of a strong acid, preferably methanesulphonic acid, which protonates the alicyclic nitrogen and thus prevents its oxidation; therefore the oxidation of the pyridine becomes primary. As an oxidant, any type of peracid, preferably peracetic acid may be used.

The optically active enantiomers of the compound of the invention are prepared by using the suitable optically active O-(3-piperidino-2-hydroxy-1-propyl)-3-pyridine hydroxymic acidchloride enantiomer as starting material, which can be produced for example according to EP 0 417 210 B1, by re-solving the racemic compound. In the course of the reaction, the chirality of the molecule is not damaged, and the resulting product has the same optical purity as the starting substance.

If desired, the N-[2-hydroxy-3-(1-piperidinyl)-propoxy]-pyridine-1-oxide-3-carboximidoyl chloride that obtained or one of its optically active enantiomers can be transformed into an acid addition salt with a mineral or organic acid, by known methods.

N-[2-hydroxy-3-(1-piperidinyl)-propoxy]-pyridine-1-oxide-3-carboximidoyl chloride, its optically active (+) or (−) enantiomer, a mixture of the enantiomers of any ratio, and the racemic compound, furthermore, the acid addition salts formed from any of the above compounds with mineral or organic acids constitute objects of the present invention. All possible geometrical isomer forms of N-[2-hydroxy-3-(1-piperidinyl)-propoxy]-pyridine-1-oxide-3-carboximidoyl chloride belong to the scope of the invention. The term "the stereoisomers of N-[2-hydroxy-3-(1-piperidinyl)-propoxy]-pyridine-1-oxide-3-carboximidoyl chloride" refers to all possible optical and geometrical isomers of the compound.

According to the invention, these compounds are applied for the treatment of pathological insulin resistance and for the treatment and prevention of pathological conditions associated with it.

A special embodiment of the invention is that these compounds are used for simultaneous treatment or prevention of chronic diabetes-induced complications, especially retinopathy, neuropathy and nephropathy, and of pathological insulin resistance and the pathological conditions associated therewith.

According to an other special embodiment of the invention, N-[2-hydroxy-3-(1-piperidinyl)-propoxy]-pyridine-1-oxide-3-carboximidoyl chloride or its stereoismers or acid addition salts thereof are used in the treatment of pathological insulin resistance and pathological conditions associated therewith it and a simultaneous increasing of a diabetes-iduced pathologically decreased peripheral neuroregeneration.

The compounds of the invention may be applied both in human and veterinary therapy.

Therefore, the object of the invention also includes the method for the treatment of pathological insulin resistance and treatment and prevention of pathological conditions associated therewith, in the course of which the patients are administered N-[2-hydroxy-3-(1-piperidinyl)-propoxy]-pyridine-1-oxide-3-carboximidoyl chloride or one of its stereoisomers in the form of base or acid addition salt. The preferred embodiment of the procedure of the invention is when N-[2-hydroxy-3-(1-piperidinyl)-propoxy]-pyridine-1-oxide-3-carboximidoyl chloride or one of its stereoisomers, or a acid addition salt thereof is administered to a patient suffering from diabetic retinopathy, neuropathy or nephropathy.

According to another special embodiment of the invention N-[2-hydroxy-3-(1-piperidinyl)-propoxy]-pyridine-1-oxide-3-carboximidoyl chloride or one of its stereoisomers or an acid addition salt thereof is administered to a patient in case of pathological decrease of neuroregeneration caused by diabetes.

The dose of the compounds depends on the condition and the disease of the patient, and the daily dose is 0.1–400 mg/kg, preferably 0.1–100 mg/kg. In human therapy, the oral dose is preferably 10–300 mg, in the case of rectal administration 1–15 mg, while in the case of parenteral administration 1–15 mg for an adult patient. These doses are preferably administered in dosage unit forms, which may be divided into 2–3 smaller doses for a day in certain cases, especially in oral treatment.

Preferably, the stereoisomer of the racemic compound, most preferably the (+) enantiomer is used. In this case, a smaller quantity of active ingredient within the above limits is sufficient for the treatment.

Pharmaceutical preparations suitable for the treatment are also object of the invention. These pharmaceutical compositions contain, in addition to the usual auxiliary substances and carriers, N-[2-hydroxy-3-(1-piperidinyl)-propoxy]-pyridine-1-oxide-3-carboximidoyl chloride or one of its stereoisomers, or an acid addition salt of one of the above, as active ingredients.

The pharmaceutical compositions of the invention can be prepared in the to form of a solid or fluid preparation generally used in human or veterinary therapy. Simple or coated tablets, dragees, granulates, capsules, solutions or syrups can be prepared for oral administration, suppositories for rectal administration, and lyophilised or not lyophilised injection or infusion solutions for parenteral administration. These can be produced by the usual methods. The products for oral use can contain filling materials such as microcrystalline cellulose, starch or lactose, lubricants such as stearic acid or magnesium stearate, coating materials such as sugar, film forming materials such as hydroxy-methyl-cellulose, aromas or sweeteners such as methyl-paraben or saccharine, or coloring substances. The suppositories can contain cocoa butter or polyethylene glycol as auxiliary. The parenteral products can contain, in addition to the effective substance, saline solution, or in certain cases dispersing and moistening substances such as propylene glycol.

The invention is further illustrated by the following examples:

EXAMPLE 1

Preparation of N-[2-hydroxy-3-(1-piperidinyl)-propoxy]-pyridine-1-oxide-3-carboximidoyl chloride (Z)-2-butenedioate (1:1).

40.4 g (0.136 mol) of N-[2-hydroxy-3-(1-piperidinyl)-propoxy]-3-pyridine-carboximidoyl chloride was dissolved in the mixture of 238 ml of glacial acetic acid and 13.0 g (0.136 mol) of methane sulphonic acid. 61.5 ml (0.591 mol) of 30% hydrogen peroxide solution was added at 60° C. The reaction mixture was stirred at 60° C. for 3.54 hours. The solution was cooled to 10° C., and then 91 ml of 0.5 M $Na_2S_2O_5$ solution was added thereto. 315 ml of water-acetic acid mixture was distilled off from the solution, 250 ml of 4 N NaOH solution was added to the residue (pH=10.55), and shaken with chloroform. The chloroform phase was washed with water, dried, treated with charcoal, and then evaporated. Water was added to the residue, and extracted with isopropyl ether and then with chloroform. The chloroform phase was dried, treated with charcoal, filtered and evaporated off. The residue was dissolved in acetone and transformed into salt with maleic acid. The precipitate was filtered, washed with acetone and dried. The product was crystallized from boiling ethanol.

Yield: 20 g (35%); Mp.: 150.5–154.5° C.; $^1$H-NMR (solvent: DMSO; reference: DMSO; v 300 MHz) [ppm]: 8.55 (s, 1H, 2-pyridine); 8.35 (d, 1H, 6-pyridine); 7.68 (d, 1H, 4-pyridine): 7.55 (m, 1H, 5-pyridine); 6.00 (s, 2H, CH═CH); 4.23–4.48 (m, 3H, C$\underline{H}$—OH and NOCH$_2$); 2.95–3.50 (m, 6H, 3×NCH$_2$); 1.20–1.90 (m, 6H, piperidine: 3×CH$_2$).

$^{13}$C-NMR (solvent: DMSO; reference: DMSO; v=300 MHz) [ppm]: 167.6 (2C, 2COOH); 141.0 (2-pyridine); 136.8 (6-pyridine); 136.4 (2C, CH═CH); 133.4 (CCl); 131.9 (3-pyridine); 127.2 (4-pyridine); 123.6 (5-pyridine); 77.9 (NOCH$_2$); 63.6 (CH$_2$N); 58.3 (CHOH); 52.0–55.0 (2C, piperidine: 2×NCH$_2$); 22.6, and 21.7 (3C, piperidine: 3×CH$_2$).

EXAMPLE 2

Preparation of (+)-/R/-N-[2-hydroxy-3-(1-piperidinyl)-propoxy]-pyridine-1-oxide-3-carboximidoyl chloride (Z)-2-butenedioate (1:1).

The procedure described in Example 1 was repeated with the difference that instead of the racemic N-[2-hydroxy-3-(1-piperidinyl)-propoxy]-3-pyridine-carboximidoyl chloride, its R enantiomer was used. The pure form of the compound was isolated from the crude base by crystallization with hexane.

Yield: 31%; Mp.: 91–93° C.; IR (KBr, cm$^{-1}$); 3167 (br); 2840; 2710; 1575; 1560; 1480; 1443 (br); 1293 (s); 1279 (s); 1093; 1053; 1043; 1023 (s); 834 (s); 810; 688.

If desired, a maleate salt can also be prepared from the crude base in acetone solution as described in Example 1.

Yield: 33%; Mp.: 132.0–133.0° C.

Enantiomer ratio, 98/2 (HPLC measurement on a Chiral AGP 100×4 mm column).

$^1$H-NMR and $^{13}$C-NMR: same as the spectra of the racemic compound.

EXAMPLE 3

Preparation of (−)-/S/-N-[2-hydroxy-3-(1-piperidinyl)-propoxy]-pyridine-1-oxide-3-carboximidoyl chloride (Z)-2-butenedioate (1:1)

The procedure in Example 1 was followed, with the difference that instead of the racemic N-[2-hydroxy-3-(1-piperidinyl)-propoxy]-3-pyridine-carboximidoyl chloride, the S-enantiomer was used.

Yield: 34%; Mp.: 132.0–133.0° C.

Enantiomer ratio: 98/2 (HPLC measurement on a Chiral AGP 100×4 mm column).

$^1$H-NMR and $^{13}$C-NMR: same as the spectra of the racemic compound.

EXAMPLE 4

| Tablet | |
|---|---|
| (+)-N-[2-hydroxy-3-(1-piperidinyl)-propoxy]-pyridine-1-oxide-3-carboximidoyl chloride | 20.0 mg |
| Corn starch | 100.0 mg |
| Lactose | 95.0 mg |
| Talc | 4.5 mg |
| Magnesium stearate | 0.5 mg |

The finely ground active ingredient was mixed with the auxiliary materials, the mixture was homogenized and granulated. The granulate was then compressed into tablets.

EXAMPLE 5

| Capsule | |
|---|---|
| (+)-N-(2-hydroxy-3-(1-piperidinyl)-propoxy]-pyridine-1-oxide-3-carboximidoyl chloride maleate | 20.0 mg |
| Microcrystalline cellulose | 99.0 mg |
| Amorphous silicium dioxide | 1.0 mg |

The active ingredient was mixed with the auxiliary materials, the mixture was homogenized and filled into gelatine capsules.

EXAMPLE 6

| Dragée | |
|---|---|
| N-[2-hydroxy-3-(1-piperidinyl)-propoxy]-pyridine-1-oxide-3-carboximidoyl chloride maleate | 25.0 mg |
| Lactose | 82.5 mg |
| Potato starch | 33.0 mg |
| Polyvinyl pyrrolidone | 4.0 mg |
| Magnesium stearate | 0.5 mg |

The active ingredient and the polyvinyl pyrrolidone were dissolved in ethanol. A mixture of the lactose and the potato starch were moistened evenly with the granulating solution of the active ingredient. After filtering, the granulate was dried at 50° C. and screened. The magnesium stearate was added and pressed into tablet form, which was then covered by a sugar coating and polished by bee wax.

EXAMPLE 7

| Suppository | |
|---|---|
| (+)-N-[2-hydroxy-3-(1-piperidinyl)-propoxy]-pyridine-1-oxide-3-carboximidoyl chloride | 4.0 mg |
| Cocoa butter | 3.5 g |
| Solid fat 50 suppository mass | 15.0 g |

The cocoa butter and the suppository mass were heated to 40° C., and the active ingredient was dispersed in the melted mixture, then the mass was filled into suppository moulds.

EXAMPLE 8

| Solution | |
|---|---|
| (+)-N-[2-hydroxy-3-(1-piperidinyl)-propoxy]-pyridine-1-oxide-3-carboximidoyl chloride hydrochloride | 500 mg |
| Sorbitol | 10 g |
| Saccharine sodium | 0.05 g |
| Bidistilled water | q.s.ad 100 ml |

EXAMPLE 9

| Injection | |
|---|---|
| (+)-N-[2-hydroxy-3-(1-piperidinyl)-propoxy]-pyridine-1-oxide-3-carboximidoyl chloride maleate | 2 mg |
| Physiological saline solution, pyrogen-free, sterile | q.s.ad 2.0 ml |

The solution was poured into 2 ml vials and then sealed.

EXAMPLE 10

Infusion solution; 500 ml of infusion solution was prepared with the following composition:

| | |
|---|---|
| N-[2-hydroxy-3-(1-piperidinyl)-propoxy]-pyridine-1-oxide-3-carboximidoyl chloride maleate | 20.0 mg |
| Physiological saline solution, pyrogen-free, sterile | q.s.ad 500 ml |

What is claimed is:

1. N-[2-hydroxy-3-(1-piperidinyl)-propoxy]-pyridine-1-oxide-3-carboximidoyl chloride, its stereoisomers, and the acid addition salts thereof.

2. A method of treating insulin resistance comprising administering to a patient at least one compound chosen from N-[2-hydroxy-3-(1-piperldinyl)-propoxy]-pyridine-1-oxide-3-carboximidoyl chloride, stereoisomers thereof, and acid addition salts thereof.

3. A method of treating insulin resistance and at least one other pathological condition resulting from secondary effect of high insulin level or a chronic diabetic complication comprising administering to a patient at least one compound chosen from N-[2-hydroxy-3-(1-piperidinyl)-propoxy]-pyridine-1-oxide-3-carboximidoyl chloride, stereoisomers thereof, and acid addition salts thereof.

4. A method according to claim 3, wherein said other pathological condition is a chronic diabetic complication.

5. A method according to claim 4, wherein said chronic diabetic complication is retinopathy, neuropathy, or nephropathy.

6. A method according to claim 3, wherein said other pathological condition is diabetic pathologically-decreased peripheral neuroregeneration.

7. A method according to claim 3, wherein said other pathological condition is diabetic pathologically-decreased peripheral neuroregeneration and a chronic diabetic complication.

8. A method according to claim 7, wherein said chronic diabetic complication is retinopathy, neuropathy, or nephropathy.

9. A pharmaceutical composition comprising a pharmaceutically acceptable carrier and a therapeutically effective amount of at least one compound chosen from N-[2-hydroxy-3-(1-piperidinyl)-propoxy]-pyridine-1-oxide-3-carboximidoyl chloride, stereoisomers thereof, and acid addition salts thereof.

10. A pharmaceutical composition according to claim 9, further comprising at least one pharmaceutically acceptable auxiliary.

* * * * *

UNITED STATES PATENT AND TRADEMARK OFFICE
CERTIFICATE OF CORRECTION

PATENT NO. : 6,649,628 B1  Page 1 of 1
DATED : November 18, 2003
INVENTOR(S) : Maria Kürthy et al.

It is certified that error appears in the above-identified patent and that said Letters Patent is hereby corrected as shown below:

<u>Column 16,</u>
Lines 41-42, please change "N-[2-hydroxy-3-(1-piperldinyl)-propoxy]-pyridine-1-oxide-3-carboximidoyl" to read -- N-[2-hydroxy-3-(1-piperidinyl)-propoxy]-pyridine-1-oxide-3-carboximidoyl --.

Signed and Sealed this

Twenty-ninth Day of June, 2004

JON W. DUDAS
*Acting Director of the United States Patent and Trademark Office*